United States Patent
Takahashi et al.

[11] Patent Number: 5,476,796
[45] Date of Patent: Dec. 19, 1995

[54] IMMUNOLOGICAL TEST METHOD

[75] Inventors: Kenji Takahashi; Makoto Nakamura, both of Hachioji, Japan

[73] Assignee: Olympus Optical Co., Ltd., Tokyo, Japan

[21] Appl. No.: 338,273

[22] Filed: Nov. 14, 1994

Related U.S. Application Data

[63] Continuation of Ser. No. 897,247, Jun. 11, 1992, abandoned.

[30] Foreign Application Priority Data

Jun. 18, 1991 [JP] Japan .................................. 3-173093

[51] Int. Cl.⁶ .................................................. G01N 33/553
[52] U.S. Cl. .......................... 436/526; 436/805; 210/222; 210/695
[58] Field of Search .................................. 436/526, 805; 210/222, 695

[56] References Cited

U.S. PATENT DOCUMENTS 4,904,391  2/1990  Freeman .................................. 210/695

FOREIGN PATENT DOCUMENTS

| | | |
|---|---|---|
| 0209490 | 1/1987 | European Pat. Off. . |
| 0339980 | 11/1989 | European Pat. Off. . |
| 0351857 | 1/1990 | European Pat. Off. . |
| 0396115A2 | 11/1990 | European Pat. Off. . |
| 3925093 | 1/1991 | Germany . |
| 2-124464 | 5/1990 | Japan . |
| 3-4170 | 1/1991 | Japan . |
| WO90/03844 | 4/1990 | WIPO . |

*Primary Examiner*—Toni R. Scheiner
*Assistant Examiner*—Susan C. Wolski
*Attorney, Agent, or Firm*—Frishauf, Holtz, Goodman, Langer & Chick

[57] ABSTRACT

A test method for determining the presence or absence of an antigen or antibody analyte in a sample. The sample is first reacted in a reaction vessel with magnetic carrier particles having immobilized thereon a substance which specifically binds to said analyte, thereby forming bound and unbound magnetic carrier particles. The bound and unbound magnetic carrier particles are then precipitated on a flat and substantially horizontal inside wall surface of said reaction vessel with a magnet provided outside the reaction vessel, such that a gradient magnetic field is formed in a plane perpendicular to a direction in which the bound and unbound magnetic particles are precipitated, thereby forming a precipitation image on the wall surface. Finally, the presence or absence of the analyte is determined by the shape of the precipitation image. The gradient magnetic field is formed by placing the magnet outside said reaction vessel such that the distance between the wall surface of the reaction vessel on which the precipitation image is formed and the surface of the magnet opposing the wall surface is gradually increased, thereby forming an effective angle between the magnet and the wall surface. The precipitation image is formed independently of the shape of the reaction vessel. When the wall surface of the vessel is flat, it is very easy to stably maintain the precipitation image after its formation.

23 Claims, 4 Drawing Sheets

IMMUNOLOGICAL TEST METHOD

This application is a Continuation of application Ser. No. 07/897,247, filed Jun. 11, 1992, now abandoned.

BACKGROUND OF THE INVENTION

1. Field of the Invention

The present invention relates to an immunological test method for diagnosing various diseases, blood typing and the like on the basis of antigen-antibody reactions.

2. Description of the Related Art

A microtiter technique of forming a precipitation image by carrier particles on the bottom surface of a reaction vessel has been conventionally popular as a method of detecting an antigen or antibody present in a specimen sample on the basis of an immunological agglutination reaction.

This microtiter technique, however, poses several problems. One of the problems is that a long period of time is required to form a precipitation image because precipitation of the carrier particles and aggregates thereof relies on gravity alone. How to achieve an agglutination reaction by causing the carrier particles to quickly precipitate is the main object to be achieved in the microtiter technique.

In order to provide a means for solving the problem, a method using a magnetic particle as a carrier and applying an external magnetic field to a reaction vessel to quickly form a precipitation image is disclosed in European Patent Application No. 0351857A2. This method using the magnetic carrier will be described with reference to FIGS. 1 to 3 below.

A microplate having a plurality of wells each having a bottom portion with a semispherical or conical recessed surface normally is used in the microtiter technique. FIG. 1A is a plan view of the microplate when viewed from above, and FIG. 1B is a side view showing the layout of the microplate and magnets when a test according to the microtiter technique is to be performed. As shown in FIGS. 1A and 1B, wells 2 formed in a microplate 1 have semispherical bottom surfaces, respectively. Disc-like magnets 4 are respectively located below the wells 2 and are fixed on a support table 3 such that the flat upper surfaces of the magnets 4 are horizontal.

An antigen or antibody is detected using the microplate having the above arrangement. A predetermined amount of a specimen sample and a predetermined amount of a reagent containing a magnetic carrier are distributed to each well 2, and an agglutination reaction is performed. A substance which specifically binds to an antigen or antibody to be detected (to be also referred to as a target substance hereinafter) is immobilized on the magnetic carrier (as described hereinbelow with respect to Example 1).

FIGS. 2A and 3A are views illustrating the principle of measurement according to the microtiter technique. FIGS. 2B and 3B are views showing precipitation images obtained by the microtiter technique.

In the microtiter technique, when a target substance is present in a specimen sample, a plurality of precipitated particles of the magnetic carrier 12 are bonded through the target substance 13 to form an aggregate, as shown in FIG. 2A. The magnetic carrier 12 constituting the aggregate forms a precipitation image uniformly spread on the well bottom surface, as shown in FIG. 2B. This image is called a positive (+) image. When no target substance is present in the specimen sample, a non-agglutinated magnetic carrier 12 is precipitated at the center of the bottom surface of each well 11, as shown in FIG. 3A. The precipitated non-agglutinated magnetic carrier 12 forms a precipitation image concentrated like a button at the center of the well, as shown in FIG. 3B. This image is called a negative (−) image. In this manner, the precipitation images formed on the bottom surfaces of the wells are observed with a naked eye or measured by an optical measuring unit to determine the positive or negative image, i.e., to determine whether an antigen or antibody to be detected is present in the specimen sample.

As described above, a magnetic carrier is used and an external magnetic field is applied to the reaction vessel to shorten the measurement time since a long measurement time is one of the problems of the microtiter technique. This prior art, however, cannot solve all the problems posed by the microtiter technique.

First, in a conventional microtiter technique, factors such as the size and definiteness of a precipitation image depend on the shape of the bottom of a reaction vessel such as a microplate. The shapes and surface areas of the bottoms of reaction vessels are often different in accordance with different manufacturers and different manufacturing lot numbers. Thus, the above factors tend to cause variations between the individual reaction vessels. When the shapes and surface areas of the bottoms of the reaction vessels associated with their volumes are different from each other, compositions, distribution amounts, carrier concentrations, and the like of samples and reagents must be changed to hold a reactivity of the system. For this reason, it is difficult to compare the determination results.

In a conventional microtiter technique, a precipitation image is formed by utilizing the inclination of the bottom surface of a reaction vessel. For this reason, the formed precipitation image tends to be broken by the weight of carrier particles, an electric repulsion force, or external forces such as a magnetic force, a centrifugal force, and a vibration. The degrees of collapse of precipitation images vary depending on the shapes of the bottoms of reaction vessels. Collapse of the precipitation image may cause a determination error such that a specimen sample which must be determined to be positive is determined to be negative, thus posing a decisive problem. Further, in the case where the average grain diameter of carrier particles is 3 µm or less, the formed precipitation image also tends to be broken due to Brownian movement of the particles.

In order to solve this problem, a precipitation image may be formed while a reaction vessel having a flat bottom surface is inclined from the horizontal direction, and the bottom surface of the reaction vessel is then reset to be horizontal. However, when the reaction vessel is moved, the liquid inside the reaction vessel is also moved or vibrated to cause carrier particles constituting the precipitation image to float again or move. Therefore, this method also has poor reliability.

SUMMARY OF THE INVENTION

It is an object of the present invention to provide an immunological test method, which does not depend on the types of reaction vessels such as a microplate, can always obtain a regular precipitation image, and is excellent in preservation of a precipitation image after its formation.

An immunological test method according to the present invention includes the steps of mixing in a reaction vessel a sample and a magnetic carrier having a surface immobilized with a substance which specifically binds to an antigen or antibody to be detected, applying a magnetic field to the reaction vessel to form a precipitation image on a wall surface of the reaction vessel, and determining whether the antigen or antibody to be detected is present in the sample in accordance with a shape of the precipitation image. A magnet having a magnetic force which can move the carrier is provided outside of the reaction vessel so as to face the wall surface thereof during or after a reaction between the antigen or antibody to be detected and the magnetic carrier. The magnet forms a magnetic field having a predetermined gradient with respect to a plane perpendicular to a direction in which the carrier is moved.

In order to distribute the strength of the magnetic field with the predetermined gradient from an arbitrary area on the wall surface on which the precipitation image is to be formed, an external magnet is arranged outside of the reaction vessel so that the distance between the surface of the magnet and the wall surface of the reaction vessel is gradually increased, or an external magnet having a gradient magnetic field outside of the reaction vessel, is used.

In the method disclosed in Published Unexamined Japanese Patent Application No. 2-124464, the precipitation image is formed with the magnetic carrier by utilizing the inclination of the wall surface of the reaction vessel in a uniform magnetic field generated by a magnet arranged so that the upper flat surface of the magnet is coincident with a horizontal plane running perpendicular to the gravity direction. For this reason, the shapes of precipitation images are different depending on the shapes of wall surfaces. To the contrary, in the method of the present invention, the strength of the magnetic field on the wall surface, on which the precipitation image is to be formed, is distributed from the arbitrary area with a predetermined gradient with respect to a plane perpendicular to a direction in which carrier particles precipitate, and the precipitation image is formed by the magnetic behavior. Therefore, regardless of the shape of the reaction vessel, a regular precipitation image can always be obtained by adjusting the distribution of the strength of the magnetic field.

According to the method of the present invention, a precipitation image is formed on the basis of the difference in strength of the magnetic field on the wall surface on which a precipitation image is to be formed. Vertical movement of the carrier particles is not required. For this reason, the wall surface on which a precipitation image is to be formed may be flat and perpendicular to the vertical direction. A precipitation image formed on such a wall surface is more stable than a precipitation image formed on the recessed bottom surface of the reaction vessel. Therefore, according to the present invention, a highly reliable immunological test can be performed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1A:
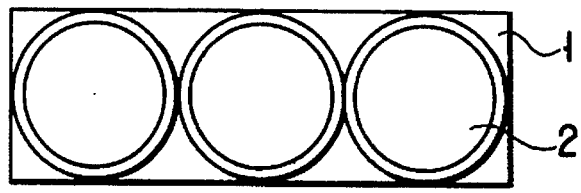
FIG. 1A is a plan view showing a conventional apparatus for practicing a microtiter technique using magnets and a magnetic carrier.

A magnetic carrier used in the present invention has a nature by which the magnetic carrier is moved toward a magnetic field generating source such as a permanent magnet or electromagnet. The shape, specific gravity, and size of the magnetic carrier are not limited to specific ones. That is, according to the present invention, a magnetic carrier having an arbitrary specific gravity and an arbitrary size can be used. For example, in order to form a precipitation image by using a carrier having a low specific gravity such as a fine particle having a particle size of 1 μm or less, or a hollow particle, a relatively strong magnetic force may be applied. When a carrier having a high specific gravity such as one having a specific gravity exceeding 1.5 is used, a relatively weak magnetic force is preferably applied.

As described above, the shape and size of the magnetic carrier are not limited to the specific ones. The magnetic carrier used in the present invention, however, is preferably a spherical or sphere-like polygonal particle having an average particle size of 0.1 to 50 μm. The magnetic substance is granular, or a polymer having a hydrophilic surface or a coacervate, which contains a predetermined amount of fine magnetic particles each having a particle size of less than 0.1 μm, can be used as such a magnetic particle. The average particle size of the magnetic carrier preferably falls within the range of 3 to 15 μm, and most preferably 5 to 10 μm in consideration of the contrast of the resultant precipitation image.

The magnetic carrier can be easily manufactured by selecting an appropriate one of the known techniques. The magnetic carrier may be colored as needed.

Examples of the inner wall surface of the reaction vessel are polystyrene, vinyl chloride, silica, carbon, gelatin, and albumin. A substance or functional group for improving the hydrophilic property or reactivity can be used as needed.

The magnet used to apply a magnetic field to the reaction vessel according to the present invention has a magnetic force capable of precipitating a magnetic carrier floating in a certain reaction solution within preferably a few minutes. Preferably, the magnet has almost a uniform magnetic force at a certain distance from its surface. The polarity of the magnet is not limited to the N or S pole and either pole has the same effect. In order to observe the process for forming a precipitation image or the formed precipitation image, the surface of the magnet which opposes the wall surface of the reaction vessel is preferably colored white, silver, or a similar color. A magnetically permeable flat mirror is preferably arranged between the reaction vessel and the magnet.

The reaction vessel used in the present invention is defined as a vessel having a wall surface capable of holding a predetermined amount of magnetic carrier and a predetermined amount of a specimen sample while the magnetic carrier reacts with the specimen sample to form a precipitation image. For example, a reaction vessel such as a microplate having a recessed portion for storing a liquid or the like, or a reaction vessel such as a slide glass for holding a sample or the like on a flat surface can be used as the reaction vessel. In the case where a precipitation image is formed on a flat plane, the focusing procedure is simplified.

The material for the reaction vessel is not limited to any specific material if the material has magnetic permeability. Examples of the material are glasses, plastics, and paper. The color of the reaction vessel is not limited to a specific color. In order to facilitate observation of the precipitation image, a transparent reaction vessel may be preferably used and a white or silver matter may be placed under the transparent reaction vessel, or the reaction vessel itself may be preferably colored in white or silver.

The material for the reaction vessel may be a material having such an ionic bonding capability enhanced by hydrogen peroxide treatment or plasma irradiation that immobilization of an antigen or antibody is facilitated. Various techniques for immobilizing an antigen or antibody are known, and any one of them can be used. A substance which specifically binds to or competes with the substance to be detected is selected as a substance immobilized in the reaction vessel. The substance subjected to immobilization is preferably immobilized without any gap in at least a precipitation image formation range of the reaction vessel wall surface. It should be noted that immobilization on the reaction vessel wall surface is not an essential element to the invention. Further, in the invention, the magnetic flux density (gauss) can be changed in accordance with the affinity between the reaction vessel wall surface and the carrier particle.

According to the method of the present invention, a magnetic field having a predetermined gradient is generated on a hypothetical plane perpendicular to the precipitation direction of the magnetic carrier. Normally, the magnetic carrier is precipitated on the bottom surface of the reaction vessel in the gravity direction in accordance with a conventional microtiter technique. In the conventional method, a magnetic field generating source such as a magnet is located below the reaction vessel such that a magnetic field has a predetermined gradient with respect to the horizontal plane. According to the method of the present invention, however, the magnetic carrier need not be vertically precipitated. That is, when a reaction solution containing a magnetic carrier and a sample is in contact with the side or upper surface of the reaction vessel, the magnet is located above or sideways relative to the reaction vessel, thereby forming a precipitation image on the side or upper surface. Some of the examples techniques for forming such a magnetic gradient are: forming the magnetic polar surface of a magnet, which generates a uniform magnetic force in the vertical direction, into a plane tilted at an appropriate angle or a curved surface having an appropriate curvature (FIGS. 4A–8); tilting the flux direction of the magnet at an appropriate angle with respect to the wall surface on which a precipitation image is formed (FIGS. 9A–10B); and providing a number of magnetic fields having different magnetic forces from each other, adjacent to the wall surface on which a precipitation image is formed (explanatory section of FIG. 6)

The present invention will be described in detail with reference to the accompanying drawings.

Figure 1B:
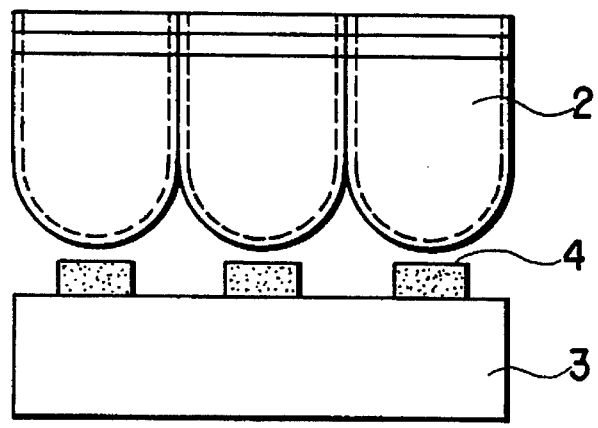
FIG. 1B is a side view of the apparatus shown in FIG. 1A.
Figure 4A:
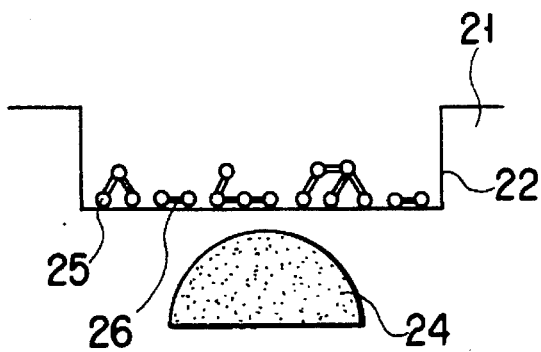
FIG. 4A is a view illustrating an apparatus for practicing a method of the present invention according to an embodiment thereof, the apparatus using a microplate having a well with a flat bottom, and a magnet having a semispherical upper surface, and also illustrating a positive reaction result obtained when a test is made using this apparatus.
Figure 4B:
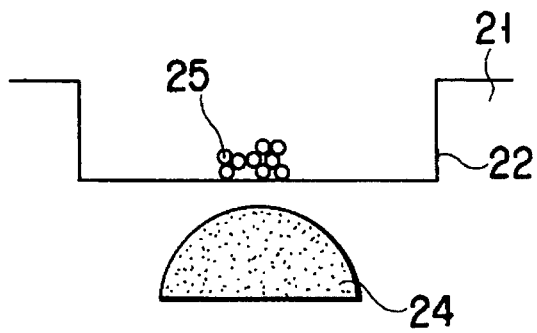
FIG. 4B is a view illustrating a negative reaction result obtained when a test is made using the apparatus shown in FIG. 4A.

FIGS. 4A and 4B are views illustrating a combination of a reaction vessel and a magnet used in the method according to an embodiment of the present invention. Referring to FIGS. 4A and 4B, a microplate 21 having a well 22 with a flat and substantially horizontal bottom is used as the reaction vessel. A semispherical magnet 24 is located below the microplate 21 so that the convex upper surface of the magnet 24 opposes the bottom surface of the well 22. The distance between the well 22 and the magnet 24 is smallest at the central point of the bottom surface of the well 22, and the distance is increased toward the periphery of the bottom surface of the well 22. The semispherical magnet 24 is a permanent magnet whose semispherical surface has an N or S pole. With this arrangement, a magnetic field is generated such that its strength is largest at the center of the bottom surface of the well 22 and the magnetic strength is gradually decreased toward the periphery. As a result, in this reaction vessel, a force directed toward the center of the well is applied to the magnetic carrier substantially in the same manner as in the conventional combination of the microplate having the well with the semispherical bottom surface and the magnet having the upper flat surface, as shown in FIGS. 1A and 1B.

Figure 2A:
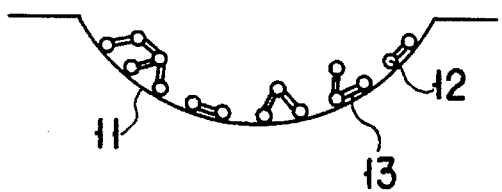
FIG. 2A is a view illustrating an aggregate of magnetic carrier, which is produced as a result of a positive reaction in the microtiter technique.
Figure 2B:
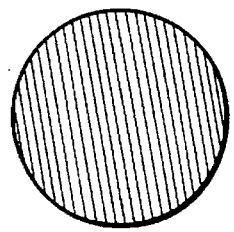
FIG. 2B is a view showing a positive image in the microtiter technique.

When a predetermined amount of a specimen sample is reacted with a predetermined amount of a magnetic carrier containing an immobilized substance which specifically binds to a target substance, and when the specimen sample contains the target substance 26, a magnetic carrier 25 agglutinated through target substance 26 is precipitated on the bottom surface of the well 22 by the magnetic field of the magnet 24, as shown in FIG. 4A. After the precipitating, the agglutinated magnetic carrier 25 is deposited without being moved along the bottom surface. As a result, a uniformly spread precipitation image is formed on the bottom surface of the well 22 as in FIG. 2A.

Figure 3A:
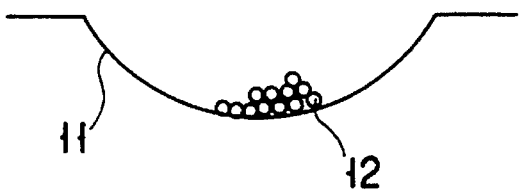
FIG. 3A is a view illustrating a magnetic carrier upon precipitating when a negative reaction is performed in the microtiter technique.
Figure 3B:
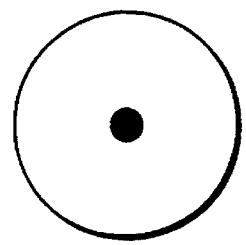
FIG. 3B is a view showing a negative image in the microtiter technique.

However, if the specimen sample does not contain the target substance, the particles of the magnetic carrier 25 are not agglutinated and are precipitated on the bottom surface of the well 22. The particles are continuously moved in a substantially horizontal direction along the bottom surface toward the central portion of the bottom surface of the well 22 because the strength of the magnetic field at the central portion is larger than that at the peripheral portion. As a result, the magnetic carrier 25 is concentrated at the central portion, thereby obtaining a precipitation image like a button as in FIG. 3B.

The curvature of the semispherical convex upper surface of the magnet 24 preferably is the same as the curvature of the inner wall of the bottom portion of the conventional well which has a semispherical recessed bottom surface.

Figure 5:
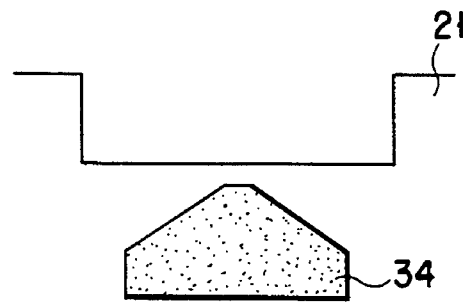
FIG. 5 is a view showing an apparatus for practicing the method according to another embodiment of the present invention, wherein the upper surface of a magnet is conical.

FIG. 5 is a view illustrating an arrangement using a magnet 34 having a shape different from that of the magnet 24 in the combination of the reaction vessel and the magnet shown in FIGS. 4A and 4B. The magnet 34 has a conical convex surface whose distal (top) end portion is slightly broken or flattened. This convex surface opposes a reaction vessel 21. The broken distal end portion is constituted by a flat surface. A non-agglutinated magnetic carrier is concentrated on a bottom surface portion of the well which opposes the flat surface, thereby forming a negative image having a specific area. Note that the apex angle of the cone constituting the convex surface of the magnet 34 preferably is similar to the apex angle of the conventional well having the conical recessed bottom surface.

Figure 6:
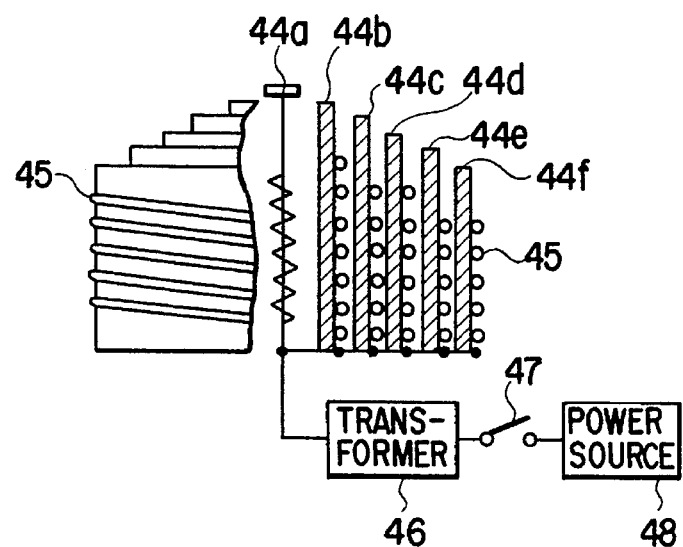
FIG. 6 is a view illustrating the structure of a magnet as an electromagnet used in the apparatus for practicing a method of the present invention according to an embodiment thereof.

FIG. 6 is a partial sectional view illustrating an electromagnet used as a magnetic field generating source instead of a permanent magnet (FIGS. 4A and 4B or 5). As shown in FIG. 6, the electromagnet comprises a rivet-like magnetic member 44a and cylindrical magnetic members 44b to 44f. The cylindrical magnetic member 44b is arranged to surround the rivet-like magnetic member 44a at a position lower than the magnetic member 44a. Similarly, the cylindrical magnetic members 44c 44d, 44e, and 44f are concentrically arranged around the magnetic member 44a so that their heights are gradually decreased outward. Windings 45 are respectively wound around the bodies of the magnetic members 44a to 44f and are connected to a power source 48 through a transformer 46 and a switch 47. When the switch 47 is turned on, the power source 48 is connected to the transformer 46. Currents flow in the windings 45 through the transformer 46, thereby equally magnetizing the magnetic members 44a to 44f.

When the electromagnet having the above arrangement is located below the microplate shown in FIGS. 4A and 4B or FIG. 5, a magnetic field is generated on the bottom surface of the well such that its strength is decreased from the center to the periphery. Therefore, a precipitation image as in the combination of FIGS. 4A and 4B can be formed.

In the electromagnet shown in FIG. 6, the windings 45 are respectively wound around the rivet-like magnetic member 44a and the cylindrical magnetic members 44b to 44f. However, the lower portions of the magnetic members 44a to 44f may be integrally formed, and a winding may be wound around this common portion to obtain the same magnetization as in the above electromagnet.

Alternatively, the upper surfaces of the rivet-like magnetic member 44a and the cylindrical magnetic members 44b to 44f may be flush with each other, and the numbers of turns of the windings 45 of the respective magnetic members may be set different from each other to electrically control the magnetic field such that its strength is decreased outwardly toward the periphery. With an electromagnet electrically controlled, the magnetic gradient can be varied without changing the shape of the upper surface of the magnet. Therefore, analysis of a number of items can be covered thereby.

Figure 7:
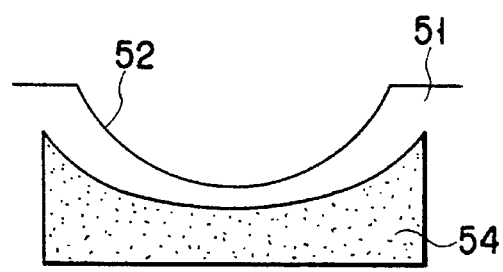
FIG. 7 is a view illustrating an apparatus for practicing the method according to still another embodiment of the present invention, wherein a reaction vessel is a microplate having a semispherical well.
Figure 8:
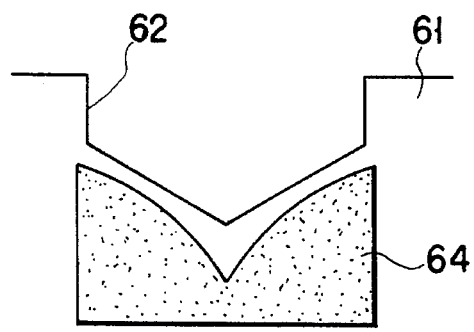
FIG. 8 is a view showing an apparatus for practicing the method according to still another embodiment of the present invention, wherein a reaction vessel is a microplate having a conical well.

FIGS. 7 and 8 are views showing microplates as reaction vessels containing wells having semispherical and conical bottom surfaces, respectively, in place of the microplate having wells with flat bottoms.

Referring to FIG. 7, a magnet 54 having one recessed surface is located below a well 52 having a semispherical inner surface in a microplate 51 so that the recessed surface of the magnet 54 opposes the well 52. The distance between the inner surface of the well 52 and the recessed surface of the magnet 54 is shortest near the center at which the inclination of the inner surface of the well is smallest. The distance is increased toward the periphery where the inclination is increased. The curvature of the recessed surface of the magnet 54 is determined in association with the curvature of the inner surface of the well 52, so that a force equal to that obtained by changing the semispherical bottom surface of the well of the microplate shown in FIG. 1B into a conical bottom surface is applied to the magnetic carrier.

Referring to FIG. 8, a magnet 64 having one recessed surface is located below a well 62 having a conical inner surface in a microplate 61 so that the recessed surface of the magnet 64 opposes the well 62. The distance between the well 62 and the recessed surface of the magnet 64 is shortest at the periphery of the well 62 as opposed to that in FIG. 7. The distance is increased toward the central portion of the well 62. The curvature of the magnet 64 is determined in association with the apex angle of the conical well 62. The same force as in the well having the semispherical bottom surface in the microplate shown in FIG. 1B is applied to the magnetic carrier.

With the arrangement shown in FIGS. 7 or 8, by using the microplate in which the shape of the bottom surface of the well is semispherical or conical, the same result as in the plate in which the shape of the well is conical or semispherical can be obtained. That is, one plate may be used as a plate having a well with a semispherical bottom surface or as a plate having a well with a conical bottom surface. When a commercially available microplate is used, differences caused by different well shapes (e.g., different manufacturers and different lot numbers) need not be taken into consideration, and compatibility can be improved.

The present invention will be described in detail below by way of an example.

EXAMPLE 1

Preparation of Plate Immobilized with Human IgG

A solution obtained by diluting a human IgG (ICN; Product No. 64-145 available from Seikagaku Kogyo KK) with a 0.01M PBS, pH 7.43 at a concentration of 15.6 µg/ml was distributed in 50 µl/well in each well of a plate having a flat bottom (2×8 wells; well diameter: 6 mm; Product No. 469914) available from NUNC Corp. and was incubated at room temperature for 30 minutes. Thereafter, the incubated solution was washed with a PBS, and the reaction products were dried naturally.

Preparation of Magnetic Particles Sensitized With Anti-Human IgG

200 µl of a suspension (particle concentration: 5% (W/W)) of magnetic gelatin particles having an average particle diameter of 6.1 µm (available from Olympus Optical Co., Ltd.) were washed with a 0.01M PBS, pH 7.43. After 1 ml of a PBS solution of tannic acid was added to the suspension, the resultant solution was incubated at 37° C. for 30 minutes. After the reaction product was washed with a 0.01M PBS solution, pH 7.43, and 1 ml of a 0.01M PBS solution (concentration: 25 µg/ml), pH 7.43, of a goat anti-human IgG antibody (available from CAPPEL Corp.) was added thereto, the resultant solution was incubated at 37° C. for an hour. After this incubation, the magnetic gelatin particles which were sensitized with the antibody were washed with a 0.01M PBS, pH 7.43. The magnetic gelatin particles were suspended to have a particle concentration of 0.25% (W/W) in a 0.01M PBS, pH 7.43 containing a 0.2% bovine serum albumin and 0.05% $NaN_3$.

Preparation of Nonsensitized Magnetic Particles

Nonsensitized magnetic particles were prepared following the same procedures as in the preparation of the magnetic particles sensitized with the anti-human IgG antibody except that the concentration of the goat anti-human IgG antibody was set to be 0 µg/ml.

Formation of Reaction Pattern

Figure 9A:
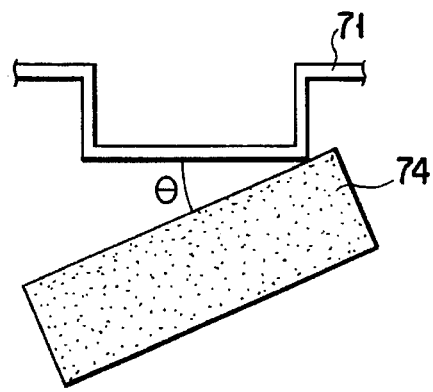
FIG. 9A is a view illustrating an apparatus using a microplate having a well with a flat bottom and a magnet having a flat upper surface according to still another embodiment of the present invention.

The prepared IgG-immobilized plate was placed horizontally, and 25 µl of the prepared antibody-sensitized particles and 25 µl of the prepared nonsensitized particles were added to and stirred in two wells, respectively, of the plate. Immediately thereafter, as shown in FIG. 9A, the plate was placed horizontally and a magnet 74 was brought into contact with one point of the periphery of the bottom surface of each well and was fixed so that an angle formed between the bottom surface of each well and the upper surface of the corresponding magnet 74 was set to be an angle θ. The magnet 74 was a columnar cast iron magnet having a flux density of about 2,000 gauss, a diameter of 24 mm and a height of 22 mm, and the angle θ was set to be 20°. In this state, the reactions of the sensitized and nonsensitized particles were continued for 5 minutes to form reaction patterns.

Figures 9B, 9C:
FIG. 9B is a view showing a positive image obtained by using the apparatus shown in FIG. 9A.
FIG. 9C is a view showing a negative image obtained by using the apparatus shown in FIG. 9A.

As a result, a positive image of the sensitized particles was a pattern almost uniformly spread on the bottom surface of the corresponding well, as shown in FIG. 9B, formed by the particles moving along the bottom wall surface in the direction of inclination of magnet 74. However, a negative image formed by the nonsensitized particles was a pattern concentrated near the point with which the corresponding magnet 74 was in contact, as shown in FIG. 9C. The same effect was obtained regardless of the polarity (N or S pole) of the surface of each magnet 74 at a position opposite to the surface of the corresponding well. In addition, the positive image formed in the flat well was stably maintained over a week even if the magnet 74 was removed from the bottom of the well.

As described above, the magnet was inclined and fixed so that the surface of the magnet was gradually separated from one point of the bottom surface of the reaction vessel having the flat bottom surface, and precipitation images having patterns unique to the positive and negative images could be formed.

Next, by following a similar procedure to the above-described example, both sensitized and nonsensitized types of magnetic particles were prepared for each of the four types of magnetic particles, differentiated from each other by average diameters. The average diameters of magnetic particles were 1.8 µm, 3.2 µm, 4.0 µm, and 6.1 µm. Immediately after adding 25 µl/ml of each of the particles to each well of a microplate, the following cases were examined:

(a) the case where the magnet 74 is brought into contact at one point with the peripheral portion of the other bottom surface of a well as shown in FIG. 9A; and (b) the case where the magnet is placed 3 mm away from the point.

Regarding these cases, the image formed 5 minutes after the magnet 74 was tilted at various angles was observed for all the types of particles, and the shapes of the obtained images were classified into 5 categories. The classification was based on the length of the image in the diameter line equally divided into 5 sections from the contact point side. Symbol (+++) represents an image of particles expanded all over the well surface, symbol (++) represents that of particles expanded to reach 4/5 of the length as shown in FIG. 9B, symbol (+) for expansion up to 3/5 of the length, symbol (±) for expansion up to 2/5 of the length, and symbol (−) for an image of particles coagulated in 1/5 or less of the length. The results were as shown in Table 1 given below, and the same results were obtained regardless of particles diameter, and did not change after letting them stand overnight.

TABLE 1

| Tilted Angle θ° | positive/negative | |
|---|---|---|
| | (a) | (b) |
| 0 < θ < 4 | +++/++ | +++/+++ |
| 4 ≦ θ < 11 | +++/± | +++/+ |
| 11 ≦ θ < 23 | ++/− | +++/± |
| 23 ≦ θ < 34 | ++/− | ++/− |
| 34 ≦ θ < 45 | +/− | +/− |
| 45 ≦ θ < 50 | ±/− | ±/− |
| 50 ≦ θ | −/− | −/− |

Regarding positive/negative in Table 1, the "positive" side indicates an image of anti-IgG antibody immobilized particles showing positive reaction, whereas the "negative" side indicates an image of nonsensitized particles showing negative reaction.

In the meantime, more images were formed by following the same procedure as in Example 1 except for changing the magnetic flux density and the area of the upper surface of the magnet. By use of a rare earth magnet having a diameter of 5 mm and a magnetic flux density of 2800 gauss, a similar image to that obtained in Example 1 was obtained, whereas by use of a rare earth magnet having a diameter of 3 mm and a magnetic flux density of 2500 gauss, positive and negative images having a diameter of 3 mm or less were formed at a desired position of the bottom surface of a well. Consequently, in the invention, regardless of the area of the wall surface of the reaction vessel, the area of the magnet can be made less than that of the wall surface of the reaction vessel. Thus, an image can be formed within such a small area that the detection sensitivity of an analyte of a small amount or a low reactivity can be enhanced.

As indicated in Table 1, it is possible to use a magnetic field having various gradients with respect to the bottom surface of the reaction vessel, and therefore the same advantages can be naturally obtained by use of magnets having circular shapes as shown in FIGS. 4–8. Further, as mentioned, clear positive and negative images can be obtained by varying the magnetic gradient, for example, after enhancing only the precipitation of the magnetic carrier.

The antibody-sensitized particles and the nonsensitized particles were added to and stirred in two wells different from the above two wells in the IgG-immobilized plate in the same manner as described above. The columnar magnet 74 was horizontally adhered to the bottom surface of each well, and the sensitized and nonsensitized particles were uniformly precipitated on the entire bottom surfaces of the respective wells within one minute, and then the corresponding magnets 74 were inclined at the predetermined angle θ for 2 minutes. As a result, positive and negative images as in the above case were formed.

The antibody-sensitized particles and the nonsensitized particles were added to and stirred in two wells different from the above pairs of wells in the IgG-immobilized plate in the same manner as described above. Magnetic particles were temporarily precipitated without applying any magnetic field thereto, and then the magnets 74 were fixed to be inclined at the predetermined angle θ. As a result, positive and negative images were formed as in the above two cases. This indicates that the method of the present invention can be applied after carrier particles were temporarily precipitated on the bottom surface of the reaction vessel by a natural settling force, a magnetic force, a centrifugal force, or the like to form the precipitation image. As a result, the above test results indicate that a precipitation image having a uniform shape can be obtained without being dependent on the shape of the reaction vessel.

The present invention is not limited to the examples described above. Various changes and modifications may be made as follows.

In Example 1, the magnet is brought into contact with one point of the periphery of the bottom surface of each well, and the inclination angle of the magnet is set to be 20°. In this case, the inclination angle is preferably less than 50° with respect to the horizontal direction or the wall surface of the reaction vessel in which a precipitation image is to be formed. When the inclination angle with respect to the wall surface of the vessel is equal to or larger than 50°, the magnetic force is greatly attenuated along the inclination, and the resultant precipitation image tends to be adversely affected by the shape of the reaction vessel. The inclination angle of the magnet applicable in the present invention, therefore, falls within the range of 4° to less than 50°, preferably 10° to 35°.

The magnet can be easily spaced apart from the bottom surface of the vessel as needed or the magnet inclination angle can be easily changed in consideration of optimum reaction times, moving characteristics of magnetic carriers, concentrations of carrier particles, compositions of suspensions, and strengths of magnetic fields. For example, by increasing the inclination angle of the magnet stepwise or continuously or largely inclining the gradient magnetic field, the formation rate of the precipitation images can be increased although the formation rate saturates at a certain point. To the contrary, by decreasing the inclination angle stepwise or continuously or moderating the inclination of the gradient magnetic field, differences in reactivity can be compared in a wider range. Therefore, a multi-purpose or multi-item test can be performed.

The size of the magnet and the strength of the magnetic field are associated with the spread areas of precipitation images to be formed. When the amount of an antigen or antibody to be detected is very small, or reactivity thereof is low due to the reasons that a specimen requires dilution in a very low concentration and a specimen is a specimen in an initial symptom, the bottom area of the reaction vessel must be reduced according to the conventional method. According to the method of the present invention, however, the size of the magnet can be reduced to reduce the size of the precipitation image so as to enhance reactivity, sensitivity, and pattern clarity without changing the bottom area of the reaction vessel.

Figure 10A:
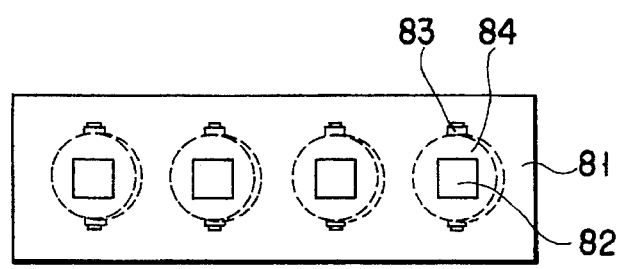
FIG. 10A is a plan view showing an apparatus for practicing the method using a flat plate having no recessed surface according to still another embodiment of the present invention.
Figure 10B:
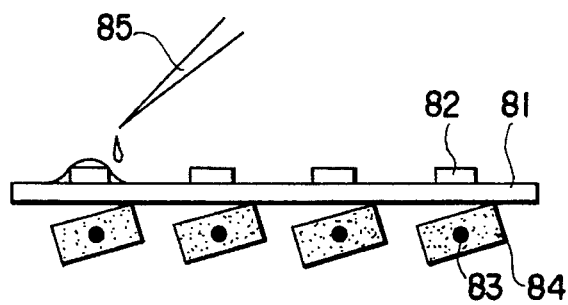
FIG. 10B is a side view of the apparatus shown in FIG. 10A.

In Example 1, a microplate having a plurality of wells is used as the reaction vessel. According to the method of the present invention, however, the reaction vessel need not have a recessed well. For example, as shown in FIGS. 10A and 10B, an apparatus for performing an agglutination reaction on a flat plate can be used. This apparatus comprises a flat plate 81 made of a magnetically permeable substance and columnar magnets 84 fixed with respect to the flat plate 81 so as to be pivotal about shafts 83. Magnets 84 are shown to have flat magnetic pole surfaces. The plurality of magnets 84 are located below the lower surface of the flat plate 81 and are spaced apart from each other. The distance between each magnet 84 and the lower surface of the flat plate 81 is set so that the magnet can be brought into contact with the flat plate 81 when the magnet 84 is pivoted. The shafts 83 extend parallel to each other, and the shafts 83 are equally spaced apart from the flat plate 81. Plate-like test pieces 82 on which precipitation images are to be formed can be detachably mounted on the upper surface of the flat plate 81 at positions immediately above the corresponding magnets 84. Each test piece 82 is placed at a predetermined position by a member (not shown) such as a projection. Each test piece 82 is made of a magnetically permeable substance (e.g., glass or plastic) which allows an antigen-antibody reaction or immobilization. The upper surface of each test piece 82 is flat and is parallel to the horizontal plane. The test pieces 82 are disposable. The pivotal operation of the magnets 84 and replacement of the test pieces 82 are performed by a pivot mechanism and a replacement unit (neither are shown).

A test using the apparatus having the above arrangement will be described as follows. Immobilization treatment on the upper surfaces of the plate-like test pieces 82 is performed following the same procedures as in Example 1, by using a pipette 85. A certain amount of each reagent containing a sample solution having a sufficient concentration of magnetic carrier particles is distributed on the respective test pieces 82, where the reagents are mixed each with other, as shown in FIG. 10B. It is suggested here that the magnetic carrier be added while maintaining the magnet 84 in a horizontal state to be applied uniformly on the test pieces 82, and then samples be brought into contact with the carrier on the test pieces 82. The magnets 84 are simultaneously pivoted in the same direction. As shown in FIG. 10B, the respective magnets 84 are brought into contact with the flat plate 81 at the same inclination angle. After a predetermined precipitating reaction of each test piece is completed, a positive or negative image as in the precipitation image shown in FIGS. 9B or 9C is formed. After the precipitation images are formed on the respective test pieces, the magnets 84 are pivoted to be parallel to the flat plate 81. An attractive force is applied to all the particles of the magnetic carrier forming the precipitation images in a direction perpendicular to the upper surfaces of the test pieces 82. The precipitation images can be stably maintained for a long period of time without breaking the patterns even if vibrations or the like are applied thereto. After completion of the optical measurement of the precipitation image, test pieces 82 alone, or the whole means including flat plate 81 and test pieces 82, are exchanged by an exchanging device, and the following analysis is performed. The flat plate 81 may be carried above the magnet 84 by a carrying device.

Regarding maintenance of precipitation images, after a lapse of a predetermined period of time from the start of formation of precipitation images according to the method of the present invention, it is effective to locate, outside the reaction vessel, a magnet having a shape or structure for applying a magnetic force always perpendicularly to the wall surface on which a precipitation image is to be formed. For example, a magnet assembly having one surface on which a compact magnet for generating a uniform magnetic field from an N or S pole is adhered on a semispherical inner surface having a radius larger than that of the semisphere constituting the inner wall of each well can be used when the wall surface on which a precipitation image is to be formed is an inner wall of a well having a semispherical bottom surface. Alternatively, when the wall surface is an inner surface of a well having a conical bottom surface, a magnet assembly on which a compact magnet is adhered to a conical recessed surface having the same apex angle in the same manner as described above can be used. In addition, when the wall surface is a flat bottom surface of a well, a magnet having a flat upper surface as described above can be used.

A precipitation image maintained by using the magnet having the above shape or structure is not limited to the formed precipitation image. That is, it is possible to maintain a precipitation image during its formation. The precipitation image formation method applied in this case is not limited to the method of the present invention but may be a conventional method using natural settling, a magnetic force, a centrifugal force, or the like.

In order to maintain a precipitation image during its formation, a magnetic carrier is precipitated by natural settling, a magnetic force, a centrifugal force, or the like. In a desired moment, a magnet having the shape or structure appropriately selected in accordance with the shape of the reaction vessel is located below the reaction vessel. At this time, magnetic carrier particles reaching the wall surface of the reaction vessel receive the magnetic force perpendicular to the wall surface and are maintained at the current positions. Magnetic carrier particles during precipitation are moved toward the nearest wall surface positions of the reaction vessel. These particles then receive the magnetic force perpendicular to the wall surface and are maintained at the current positions. As a result, the precipitation image during formation can be almost faithfully maintained as a whole.

As described above, when the magnet is located below the reaction vessel after formation of the precipitation image, all the magnetic carrier particles constituting the precipitation image receive the magnetic force perpendicular to the wall surface, and the precipitation image is stabilized.

The method of stabilizing and maintaining the image described above is most effective when the antigen or antibody is coated on the wall surface of the reaction vessel, as described above. It this case, it is possible to stabilize the precipitation image for a long period of time even if a magnetic field is applied for a relatively short period of time.

When stabilization continues for a long period of time, e.g., half a day or more, it is preferable to place the reaction vessel at a relatively high humidity or to adhere a seal to the opening of the reaction vessel, thereby preventing evaporation of the solution in the reaction vessel.

According to the method of the present invention, the shape of the magnet or the distribution of the strength of the magnetic field can be appropriately corrected without departing from the spirit and scope of the invention. For example, since a nonuniform magnetic field tends to be generated at a portion corresponding to the edge of the magnet, a magnet having an area sufficiently larger than that of the bottom surface of the reaction vessel can be used.

Further, in the above examples, a horizontal cross section of the magnet has a circular shape, but it can be a polygon if desired. For example, in Example 1, the magnet (FIG. 9A) the flux direction of which is inclined with respect to the reaction vessel wall surface, can be fan-shaped, or triangular in cross section. The composite magnet having a projecting portion on the top, formed by combining a number of cylindrical magnets with each other, as shown in FIG. 6, is not essential to the invention. A circular cone or a polygonal cone having a convex or concave surface portion at the top thereof can be prepared by point-symmetrically assembling a number of magnet blocks each having a fan-shaped or triangular cross section, in place of cylinders, thereby exhibiting a similar advantage to those of the magnets shown in FIGS. 4–8. The magnet can have a magnetic field forming surface which is concentrically circular convex or concave.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A test method for determining the presence or absence of an antigen or antibody analyte in a sample comprising the steps of:

reacting said sample in a reaction vessel with magnetic carrier particles having immobilized thereon a substance which specifically binds to said analyte, thereby forming bound and unbound magnetic carrier particles;

precipitating said bound and unbound magnetic carrier particles on a flat and substantially horizontal inside wall surface of said reaction vessel with a magnet provided outside said reaction vessel, such that a gradient magnetic field is formed in a plane perpendicular to a direction in which said bound and unbound magnetic particles are precipitated, thereby forming a precipitation image on said wall surface; and determining the presence or absence of said analyte by the shape of said precipitation image.

2. The test method of claim 1, wherein said gradient magnetic field is formed by placing said magnet outside said reaction vessel such that the distance between said wall surface of said reaction vessel on which said precipitation image is formed and the surface of said magnet opposing said wall surface is gradually increased, thereby forming an effective angle between said magnet and said wall surface.

3. The test method of claim 2, wherein said effective angle is formed by placing a magnet with a flat surface which generates a uniform magnetic force, at an angle with respect to said wall surface on which said precipitation image is formed.

4. The test method of claim 2, wherein said magnet comprises a rivet-shaped central magnetic member with a number of cylindrical magnetic members concentrically arranged around said rivet-shaped central magnetic member, wherein the height of each of said cylindrical magnetic members progressively decreases as the distance from said rivet-shaped central magnetic member increases, thereby forming a convex surface with respect to said wall surface on which said precipitation image is formed.

5. The test method of claim 2, wherein said effective angle is between 4° and 50°.

6. The test method of claim 5, wherein said effective angle is between 10° and 35°.

7. The test method of claim 3, wherein said effective angle is between 4° and 50°.

8. The test method of claim 7, wherein said effective angle is between 10° and 35°.

9. The test method of claim 1, wherein said magnet is an electromagnet.

10. The test method of claim 1, wherein the surface of said magnet opposing said wall surface of said reaction vessel on which said precipitation image is formed is colored to enhance observation of said precipitation image.

11. The test method of claim 1, wherein a magnetically permeable flat mirror is arranged between said reaction vessel and said magnet.

12. The test method of claim 1, wherein the surface of said magnet opposing said wall surface of said reaction vessel on which said precipitation image is formed has an area larger than that of said wall surface.

13. The test method of claim 1, wherein the surface of said magnet opposing said wall surface of said reaction vessel on which said precipitation image is formed has an area smaller than that of said wall surface.

14. The test method of claim 1, wherein said substance which specifically binds to said analyte is immobilized on said reaction vessel as well as said magnetic carrier particles.

15. The test method of claim 2, wherein said magnet is in the shape of a circular or polygonal cone formed from a composite of magnetic members having a fan-shaped or triangular cross section.

16. A test method for determining the presence or absence of an antigen or antibody analyte in a sample comprising the steps of:

reacting said sample in a reaction vessel with magnetic carrier particles having immobilized thereon a substance which specifically binds to said analyte, thereby forming bound and unbound magnetic carrier particles;

precipitating said bound and unbound magnetic carrier particles on a flat and substantially horizontal inside wall surface of said reaction vessel either during or after reaction of said sample and said magnetic carrier particles with a precipitating magnet provided outside said reaction vessel which produces a uniform magnetic field, thereby temporarily forming a uniform distribution of said magnetic carrier particles on said wall surface;

forming a precipitation image on said wall surface with an image-forming magnet provided outside said reaction vessel, such that a gradient magnetic field is formed in a plane perpendicular to a direction in which said bound and unbound magnetic particles are precipitated; and determining the presence or absence of said analyte by the shape of said precipitation image.

17. The test method of claim 16, wherein said gradient magnetic field is formed by placing said image-forming magnet outside said reaction vessel such that the distance between said wall surface of said reaction vessel on which said precipitation image is formed and the surface of said image-forming magnet opposing said wall surface is gradually increased, thereby forming an effective angle between said image-forming magnet and said wall surface.

18. The test method of claim 17, wherein said image-forming magnet has a flat surface and generates a uniform magnetic force and said effective angle is formed by placing said image-forming magnet at an angle with respect to said wall surface on which said precipitation image is formed.

19. The test method of claim 17, wherein said effective angle is between 4° and 50°.

20. The test method of claim 19, wherein said effective angle is between 10° and 35°.

21. The test method of claim 18, wherein said effective angle is between 4° and 50°.

22. The test method of claim 21, wherein said effective angle is between 10° and 35°.

23. The test method of claim 16, wherein said substance which specifically binds to said analyte is immobilized on said reaction vessel as well as said magnetic carrier particles.

* * * * *